United States Patent [19]
Poddar

[11] Patent Number: 5,102,413
[45] Date of Patent: Apr. 7, 1992

[54] INFLATABLE BONE FIXATION DEVICE

[76] Inventor: Satish B. Poddar, 2315 Spring Garden Dr., Bluefield, W. Va. 24701

[21] Appl. No.: 612,460

[22] Filed: Nov. 14, 1990

[51] Int. Cl.$^5$ .............................................. A61B 17/56
[52] U.S. Cl. ........................................ 606/62; 606/63
[58] Field of Search ................. 606/62, 63, 64, 60, 606/67, 68; 128/87 R, 82, 90, DIG. 20, 89 R; 446/220; 600/29-31

[56] References Cited

U.S. PATENT DOCUMENTS

| | | | |
|---|---|---|---|
| 3,812,841 | 5/1974 | Isaacson | 600/29 |
| 3,879,887 | 4/1975 | Brookson | 446/220 |
| 3,993,056 | 11/1976 | Rubischong | 128/89 R |
| 4,169,467 | 10/1979 | Rabischong | 128/89 R |
| 4,313,434 | 2/1982 | Segal | 606/62 |
| 4,799,914 | 1/1989 | Hutchinson | 446/220 |

Primary Examiner—Robert A. Hafer
Assistant Examiner—Michael Brown
Attorney, Agent, or Firm—Jones, Tullar & Cooper

[57] ABSTRACT

A device for intramedullary fixation of a fractured bone is disclosed. The device includes an elongate support rod and an inflatable bladder which is attached to the support rod and includes a plurality of bone-contacting surfaces. The device is inserted into the medullary cavity of the broken bone and the bladder is inflated to expand the bladder and extend the bone-contacting surfaces to the inner wall of the bone, where they adhere to and stabilize the bone.

11 Claims, 3 Drawing Sheets

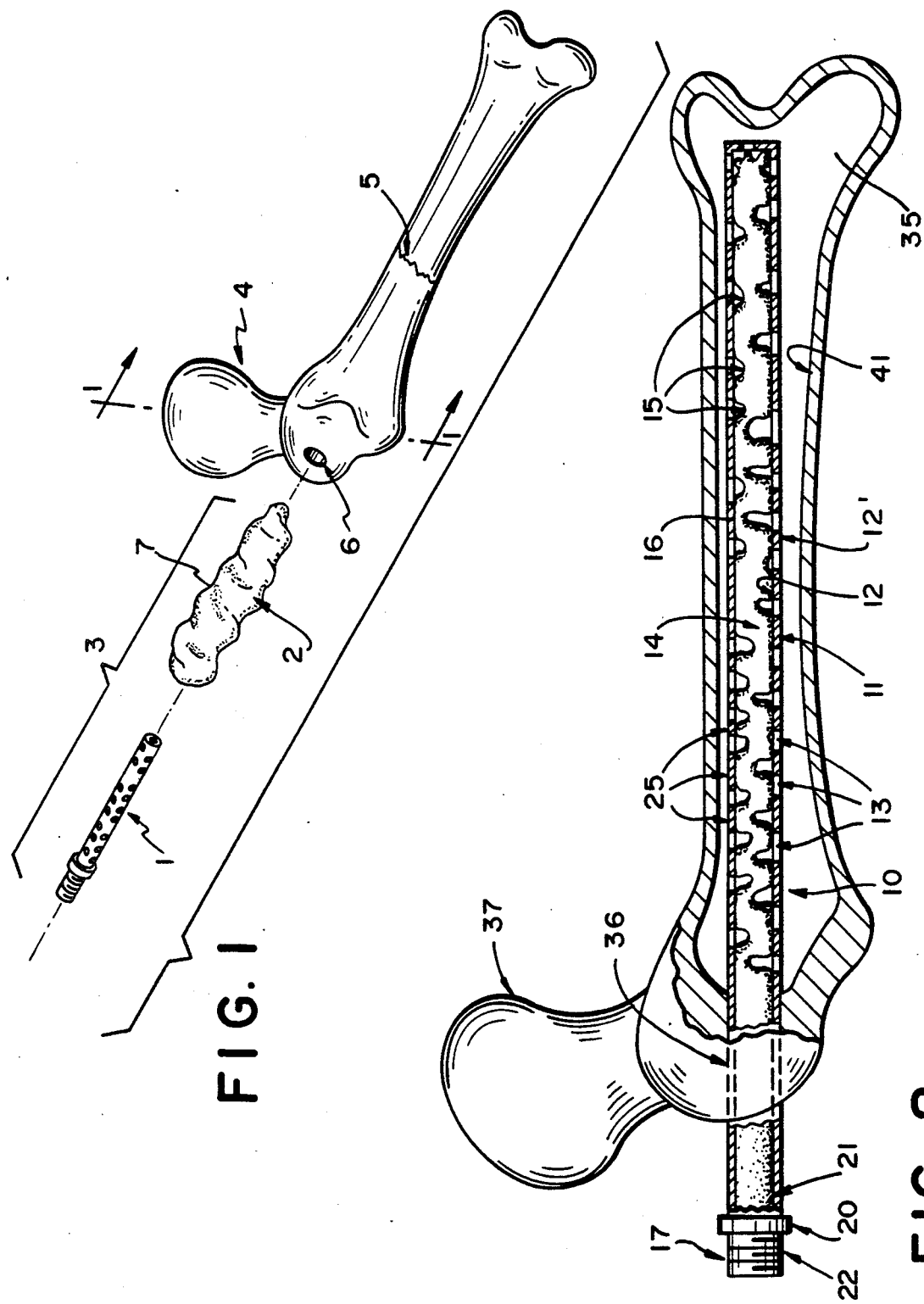

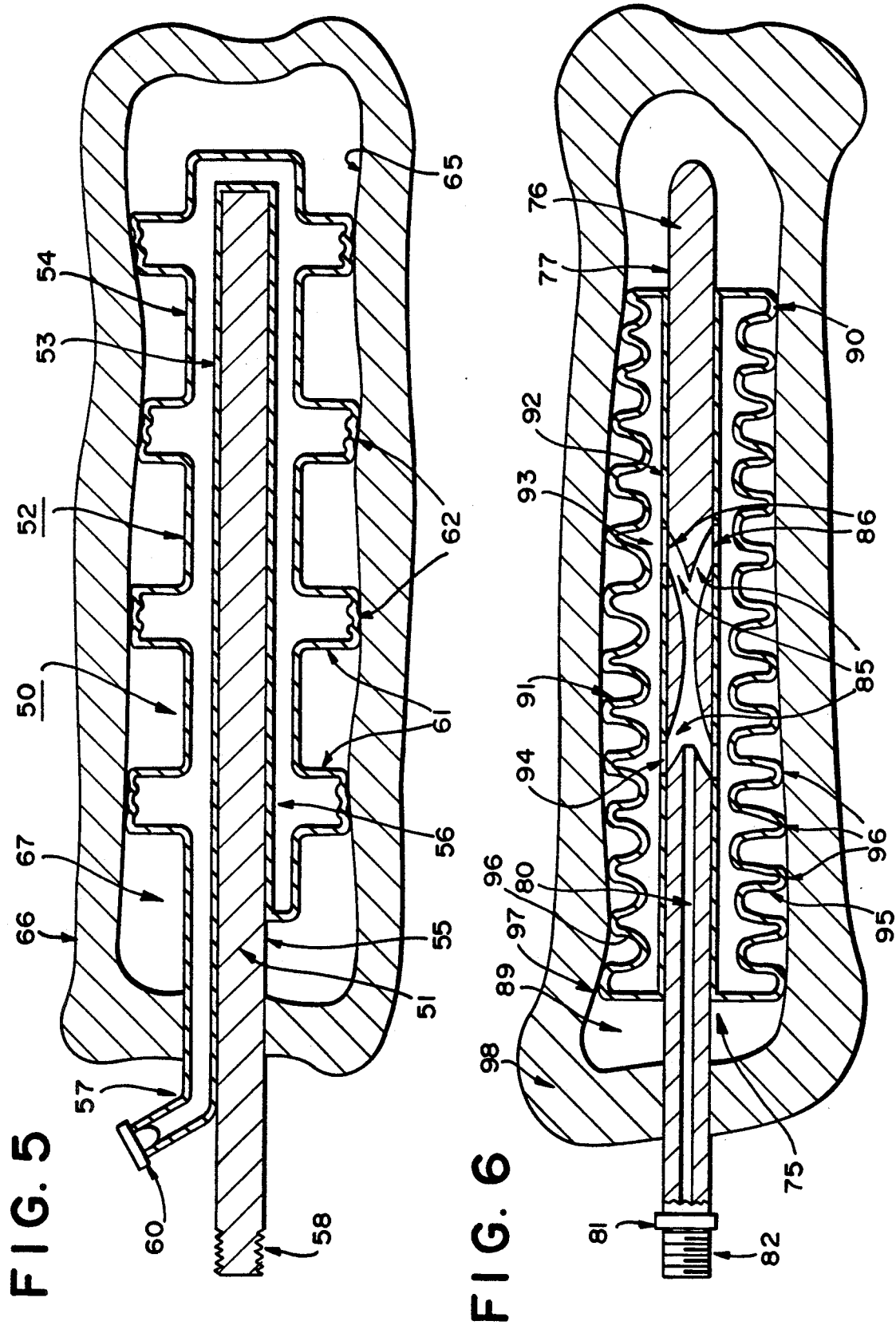

5,102,413

INFLATABLE BONE FIXATION DEVICE

FIELD OF THE INVENTION

The present invention is directed, in general, to apparatus for the intramedullary stabilization of a broken bone, and more particularly to such apparatus which includes a stabilizing rod and an inflatable, flexible bladder. More specifically, the present invention is directed to a stabilizing rod and an inflatable flexible bladder which cooperate to produce limited contact between the inflatable, flexible bladder and the intramedullary cavity of a broken bone at a plurality of predetermined locations for stabilizing the bone.

DESCRIPTION OF THE PRIOR ART

Human beings, in their many work and leisure pursuits, are, unfortunately, often subject to the possibility of accidental injury. Physical labor often involves many situations in which this danger arises. After work, many people engage in sports or other activities in order to achieve a desired level of fitness, and such activities can result in injury. Even if an "active" lifestyle is not maintained, the threat of accidental injury exists and often arises in normal daily activities such as walking, housekeeping or driving an automobile.

One of the more serious injuries that a human can endure is the breaking of one or more bones. Obviously, a bone break is initially an extremely painful and debilitating injury; however, its effects can continue long past the initial injury. For example, if the bone mends improperly along the break line, a healed but weakened bone structure results. Further, infection can set in and delay the healing process. Even the normal healing process unfortunately takes a long time, preventing the accident victim from pursuing his or her usual activities.

The prior art has attempted to provide a number of methods and/or devices for assisting and expediting the healing process of broken bones. The most common prior art device includes a thick rod, or a plurality of thinner rods, which are implanted into the medullary cavity of the broken bone to stabilize the placement of the bone fragments once they are set in place. In order for these rods to function properly upon implantation, however, they must fit tightly within the medullary cavity. This fit is usually achieved by boring or "reaming" the cavity to obtain a constant diameter, widened cavity in which the rod is inserted.

This procedure is obviously damaging to the bone structure, and destroys the inner lining of blood vessels which exist in the bone. Further, the damage caused by the reaming procedure precludes the use of this process on children, as the destruction of the inner lining disrupts or even stops growth.

Another procedure described in the prior art includes the use of an inflatable bladder as disclosed in U.S. Pat. No. 4,313,434 to Segal. However, the device described in that patent has at least two serious drawbacks. A first and important disadvantage is caused by the fact that in Segal, bone fixation is achieved by placing a bladder in the medullary cavity of a broken bone and pressurizing the bladder in its entirety to exert pressure along the entire length of the medullary cavity. This pressure can produce extreme pressure necrosis of endosteum along the entire length of the broken bone. A second disadvantage is the overall strength of the fixation bladder, for as disclosed in Segal, the device includes only a flexible, inflatable bladder which may fail under stress or extended physiological load.

A need, therefore, exists for a bone fixation device which imparts strength and stability to a broken bone during the healing process without causing substantial damage to the bone by its implantation.

BRIEF SUMMARY OF THE INVENTION

It is an object of the present invention to provide an intramedullary bone fixation apparatus which avoids the problems of prior such devices.

Another object of the present invention is to provide apparatus for intramedullary bone fixation which contacts the inner wall of the bone adjacent the medullary cavity only at specified predetermined regions and thereby reduces the likelihood of extensive bone necrosis.

A further object of the present invention is to provide a device for intramedullary bone fixation which imparts stability and strength to a healing broken bone while yet another object of the present invention is to provide a device for intramedullary bone fixation which causes little to no damage to the broken bone during implantation.

Still another object of the present invention is to provide a device for intramedullary bone fixation which enhances healing and decreases the threat of infection.

Yet still another object of the present invention is to provide a device for intramedullary bone fixation which is relatively inexpensive to produce and easy to install.

These objectives are achieved by the present invention through the use of an elongate support rod and an inflatable, flexible bladder which has at least one bone-contacting surface or region, and which is attached to and carried by the support rod for placement in the bone. The fixation device is utilized in the medullary cavity of a broken bone where it stabilizes and fixes the bone fragments, thereby assisting and expediting the healing process. The fixation device is inserted into the medullary cavity of the broken bone and extends past the region of the break in the bone so as to span the break. Thereafter, the bladder is inflated, extending discrete, spaced bone-contacting surfaces of the bladder outward from the support rod to contact the bone. These spaced surfaces preferably are formed at the ends of fingers formed in the wall of the bladder, and may include an adhesive layer which adheres to the bone upon contact of the surface with the bone. As the bladder contacts the bone only at the predetermined locations of the fingers, or bone-contacting surfaces, the bone is adequately stabilized without applying pressure to the entirety of the bone, thereby avoiding necrosis. The rod supports and positions the bladder and stiffens the fragmented bone to assist in stabilizing the bone.

BRIEF DESCRIPTION OF DRAWINGS

While the novel features of the bone fixation device of the present invention are set forth with particularity in the appended claims, a full and complete understanding of the invention may be had by referring to the following detailed description thereof, and as illustrated in the accompanying drawings, in which:

FIG. 1 is an exploded view, in perspective, of a bone fixation device in accordance with the present invention, including a support rod and an inflatable bladder and a fractured bone in which the device is to be implanted;

FIG. 2 is a partial cross-sectional view of a first embodiment of the bone fixation device of FIG. 1 as assembled and implanted, taken along line 1—1 of FIG. 1, with the inflatable bladder in a deflated state;

FIG. 5 is a cross-sectional view, taken along line 1—1 of FIG. 1, of a second embodiment of the bone fixation device of the present invention as assembled and implanted with the inflatable bladder in an inflated state; and FIG. 6 is a cross-sectional view, taken along line 1—1 of FIG. 1, of a third embodiment of the bone fixation device of the present invention as assembled and implanted, with the inflatable bladder in an inflated state.

DESCRIPTION OF THE PREFERRED EMBODIMENTS

Figures 3, 4:
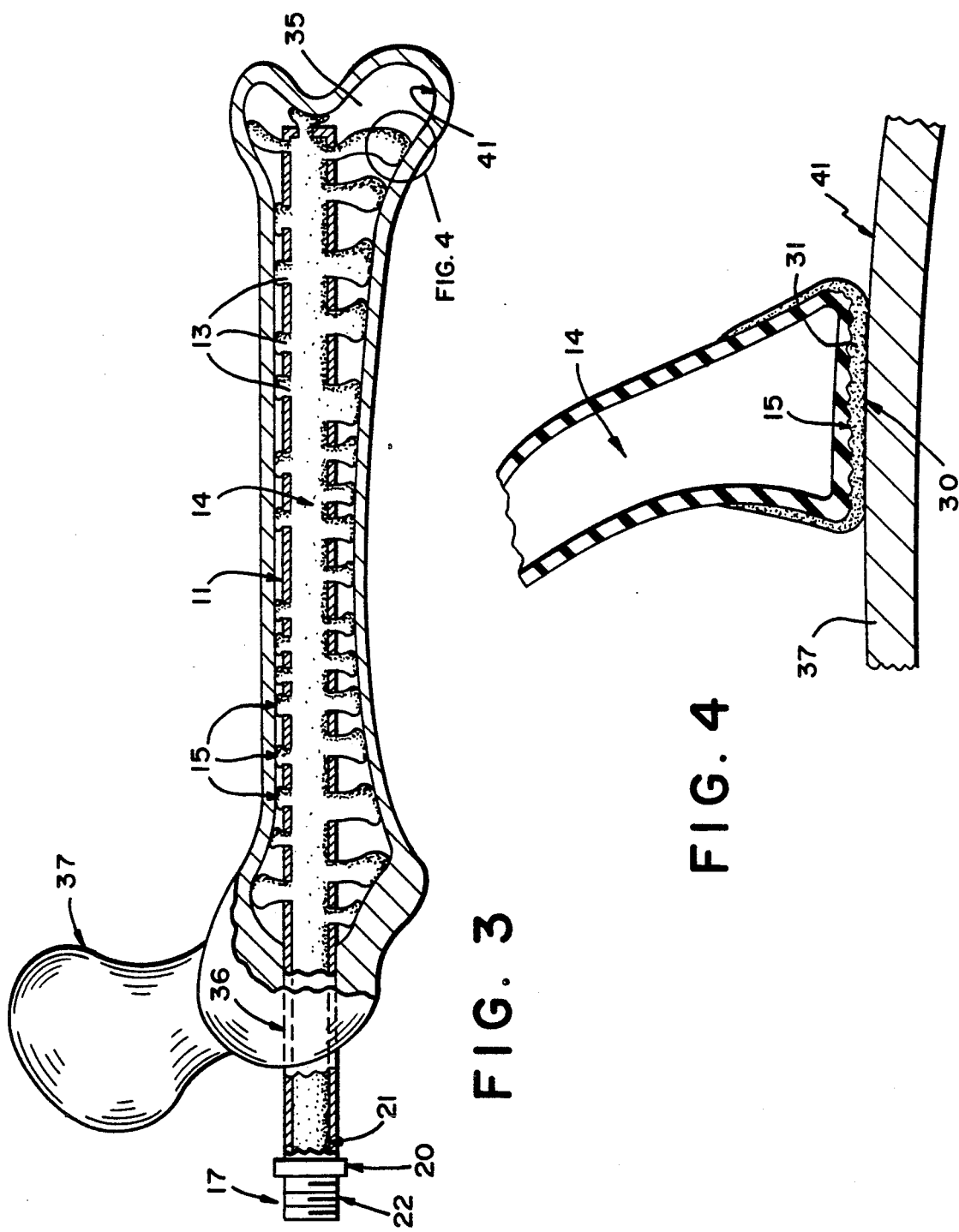
FIG. 3 is a partial cross-sectional view, taken along line 1—1 of FIG. 1, of the first embodiment of the bone fixation device of FIG. 1 assembled and implanted, with the inflatable bladder in an inflated state.
FIG. 4 is an enlargement of the circled portion of FIG. 3.

A bone fixation device in accordance with the present invention is illustrated in its most general form in FIG. 1, and includes a support rod 1 and a flexible, inflatable bladder 2. The rod is preferably formed from any material providing sufficient strength and support to a bone which is to be supported, and this preferably is metal such as stainless steel, while the bladder is an elastic or elastomeric material which may be inflated under pressure, and which will deflate when the pressure is released. In use, the bone fixation assembly 3, which includes the support rod 1 and the bladder 2, is assembled, as will be explained below, and the assembly is inserted into the medullary cavity of a bone 4 along the longitudinal axis of the bone. The bone 4 is illustrated as having been fractured or broken along a fracture line 5, and the fixation assembly 3 is sufficiently long to span the region of the break. The assembly 3 is inserted through a small opening 6 formed in the bone 4 and passes along the central longitudinal cavity of the bone. After careful positioning of the assembly the flexible bladder 2 is inflated to stabilize the bone.

A preferred embodiment of the device of the present invention is shown in FIGS. 2 and 3. The bone fixation assembly 10 of FIGS. 2 and 3 includes a support rod 11 which is hollow, having an inner surface 12 and an outer surface 12' and at least one bladder aperture 13 formed therein. In a preferred form of the invention, a plurality of apertures 13 are spaced along the length of the rod 11, and are spaced around its circumference either in a regular pattern or in a random arrangement. The apertures preferably are round, but may be oval or otherwise shaped. The assembly 10 further includes a flexible, inflatable bladder 14 contained within the interior of the rod. The bladder includes at least one bone-contacting surface 15 formed in its outer surface 16, and preferably has one for each aperture in the rod. The bladder 14 is contained within the support rod 11 in a deflated state to facilitate insertion of the assembly into the bone, with the bladder extending the length of the rod. The proximal end 17 of the support rod 11 contains a leak-proof valve 20 sealed to the support rod 11 and to the proximal end 21 of the bladder. The outer surface 22 of the proximal end 17 of the support rod 11 is preferably threaded to allow for easy implantation and extraction.

The flexible bladder 14 may be adhered by a suitable adhesive to the inner surface 12 of the support rod 11 along some or all of the rod-contacting surfaces 25 between apertures 13, or the elastomer of the bladder 14 may have adhesive characteristics, so that the bladder is held in place with the bone-contacting regions or surfaces 15 of the bladder 14 aligned with the apertures 13. The surfaces 15 may be smooth, but preferably are serrated or ridged, and in one form, the surfaces 15 may be coated at a contact area 30 with an adhesive layer 31, illustrated in FIG. 4. Alternatively, the surfaces may be made of an adhesive material or the elastomeric material of the bladder may have adhesive characteristics.

The device of the present invention, as disclosed in this preferred embodiment, is utilized by inserting the assembly 10 into the medullary cavity 35 through a small opening 36 formed in the bone 37. After insertion of the assembly 10, a pressurized expansion fluid is introduced into the bladder 14 through the valve 20. The fluid should be sterile and may include gases such as air, oxygen, or nitrogen, or may include various liquids. As the fluid expands the bladder 14 against the inner surface 12 of the rod, the bone-contacting surfaces 15 of the bladder 14 begin to extend through the bladder apertures 13 in the rod 11, while the rod-contacting surfaces 25 of the bladder 14 between the regions 15 contact the inner surface 12 of the support rod 11 and adhere thereto. The bone-contacting surfaces 15 continue to expand outwardly as the expansion fluid is introduced into the bladder 14, to form fingers which eventually engage the inner wall 41 of bone 37 adjacent the medullary cavity 35. Pressure is thereby exerted by the bone-contacting surfaces 15 of the finger portions of the bladder 14 on the bone 37 at predetermined, spaced-apart surface locations. The limited, specified locations of the pressure regions greatly decreases the risk of extensive necrosis of endosteum. The pressure is retained on the assembly 10 to hold the bladder in place, with the bladder fingers in contact with wall 41, and if an adhesive is used, that assists in holding the fingers in place.

Upon healing of the bone fracture, the assembly 10 may be removed simply by deflating the bladder 14 to release the bladder fingers, and then retracting the assembly 10 out of the bone. The adhesiveness of the bone-contacting surfaces 15 is preferably sufficient to produce adhesion only when the surfaces engage the bone 37 under pressure.

A second embodiment of the present invention is illustrated at FIG. 5. In this embodiment, the bone fixation assembly 50 includes a support rod 51 which may be tubular and closed at the distal end or may be solid. A bladder 52 surrounds the rod 51 and includes an inner wall 53 and a concentric outer wall 54 which are spaced to form a thin inflation channel 56. The proximal end 57 of bladder 52 includes a leak-proof valve 60. The inner wall 53 of bladder 52 is adhered to the peripheral surface 55 of the support rod 51 by a suitable adhesive while the outer wall 54 includes a plurality of bone-contacting fingers 61 having bone contacting surfaces or regions 62 and which may be of a thickness slightly less than the thickness of the remainder of the outer wall 54. The end 58 of rod 51 is preferably threaded.

In use, assembly 50 is inserted into the medullary cavity as discussed previously to position the rod and bladder to span the fracture in the bone. A sterile expansion fluid is introduced into the inflation channel 56 through valve 60 to inflate the bladder 52 and expand its outer wall 54. Expansion fluid introduction is continued until bone-contacting surfaces 62 contact the inner wall 65 of bone 66 adjacent medullary cavity 67. As discussed previously, bone-contacting surfaces 62 are preferably serrated and, in one form, include an adhesive layer of adhesiveness sufficient to adhere to the inner wall 65 of bone 66 upon expansion of the bladder 52, but to release from the bone 66 upon deflation of the bladder 52.

A third embodiment is illustrated in FIG. 6, wherein a rod and bladder bone fixation assembly 75 includes a support rod 76 which includes an outer wall 77, an inflation channel 80 extending longitudinally through the center of the rod 76, and a leak-proof valve 81 at the threaded, proximal end 82 of the rod 76. The inflation channel 80 incorporates a plurality of inflation branches 85 which extend radially outwardly from the inflation channel 80 of the rod 76 to form inflation apertures 86 in the surface of the outer wall 77.

An inflatable bladder 90 includes an outer wall 91 and an inner wall 92 in which bladder apertures 94 are formed. The outer wall 91 and inner wall 92 define a bladder cavity 93. Bladder apertures 94 are substantially aligned with inflation apertures 86 in rod 76 and the inner wall 92 is adhered to the outer wall 77 of rod 76 by a suitable adhesive. The bladder outer wall 91 includes at least one bone-contacting finger 95 having bone-contacting surface 96 and which may be of a thickness slightly less than the remainder of the outer wall.

In use, the assembly 75 is inserted into the medullary cavity 89 as discussed previously. A suitable expansion fluid, which is introduced into the inflation channel 80 through the valve 81, travels through the inflation channel 80, the inflation branches 85, the inflation apertures 86 and the bladder apertures 94 into the cavity 93 between the outer wall 91 and the inner wall 92 of the bladder 90. Bone-contacting fingers 95 expand upon introduction of the fluid and bone-contacting fingers contact the inner wall 97 of the bone 98 adjacent the medullary cavity 8g. As discussed previously, bone-contacting surfaces 96 are preferably serrated and include an adhesive layer of adhesiveness sufficient to adhere to the inner wall 97 of bone 98 upon expansion of the bladder 90 but to release from the bone 98 upon deflation of the bladder 90.

While the bone fixation device has been described in detail, it is to be understood that various changes and modifications may made without departure from the spirit and scope of the invention. For example, the materials utilized in the construction of the support rod and the bladder of the present invention may be any materials which provide the necessary characteristics to perform the functions heretofore described. Further, the outer surfaces of the rod and/or the bladder which are adjacent the bone may be treated with antibiotics or other compounds which enhance healing or fight infection. Also, the size of the device could be varied to provide utility for a variety of human and animal bone fractures.

What is claimed is:

1. An intramedullary bone fixation device comprising:
   (a) an elongate hollow support rod having at least one aperture formed therein;
   (b) an inflatable bladder disposed within said support rod, said bladder including at least one bone-contacting surface which extends through said aperture and contacts said bone when said bladder is inflated; and
   (c) means for inflating said bladder.

2. A device in accordance with claim 1 wherein said bone-contacting surface is serrated.

3. A device in accordance with claim 2 further comprising an adhesive layer applied to each of said bone-contacting surfaces.

4. An intramedullary bone fixation device comprising:
   (a) an elongate support rod having an outer surface, said rod including an inflation channel and a plurality of inflation apertures each connected to said inflation channel;
   (b) an inflatable bladder including a inner wall and an outer wall, said inner wall adhered to said outer surface of said support rod and including a plurality of bladder apertures each in substantial alignment with one of said inflation apertures, and said outer wall including at least one bone-contacting surface for contacting said bone when said bladder is inflated; and
   (c) means for inflating said bladder.

5. A device in accordance with claim 4 wherein said bone-contacting surface is serrated.

6. A device in accordance with claim 5 further including an adhesive layer applied to each of said bone-contacting surfaces.

7. An intramedullary bone fixation device comprising:
   (a) an elongate support rod;
   (b) an inflatable bladder carried by said support rod, said bladder including at least one bone-contacting region for contacting said bone when said bladder is inflated, said bone-contacting region being serrated when said bladder is inflated;
   (c) an adhesive layer applied to each of said bone-contacting regions; and
   (d) means for inflating said bladder.

8. An intramedullary bone fixation device comprising:
   (a) an elongate support rod;
   (b) an inflatable bladder carried by said support rod, said bladder including at least one bone-contacting region for contacting said bone when said bladder is inflated and said support rod including a longitudinal channel for receiving said bladder and at least one aperture aligned with said bone-contacting region through which said region expands when said bladder is inflated; and
   (c) means for inflating said bladder.

9. An intramedullary bone fixation device comprising:
   (a) an elongate support rod;
   (b) an inflatable sleeve surrounding said rod, said sleeve including at least one bone-contacting region for contacting said bone when said bladder is inflated; and
   (c) a means for inflating said bladder, said means including a longitudinal channel in said rod.

10. An intramedullary bone fixation device comprising:
    (a) an elongate support rod;
    (b) an inflatable bladder carried by said support rod, said bladder including at least one bone contacting region which is expandable to form a bone support finger for contacting said bone when said bladder is inflated, and (c) means for inflating said bladder.

11. An intramedullary bone fixation device comprising:

(a) an elongate support rod;

(b) an inflatable bladder having an inner wall attached to said support rod and an outer wall, said outer wall including at least one serrated bone-contacting region formed therein;

(c) an adhesive layer applied to each of said bone-contacting regions; and (d) means for inflating said bladder.

* * * * *